United States Patent
Bhartia et al.

(10) Patent No.: US 9,290,433 B2
(45) Date of Patent: Mar. 22, 2016

(54) SINGLE STAGE LUTEIN ESTER EXTRACTION FROM TAGETES SPECIES-MARIGOLD FLOWER MEAL

(75) Inventors: Uma Shankar Bhartia, New Delhi (IN); Gopu Bala Show Reddy, Noida (IN)

(73) Assignee: INDIA GLYCOLS LIMITED, Udham Singh Nagar (IN)

( * ) Notice: Subject to any disclaimer, the term of this patent is extended or adjusted under 35 U.S.C. 154(b) by 268 days.

(21) Appl. No.: 13/979,972

(22) PCT Filed: Jan. 12, 2012

(86) PCT No.: PCT/IN2012/000033
§ 371 (c)(1),
(2), (4) Date: Sep. 27, 2013

(87) PCT Pub. No.: WO2012/098559
PCT Pub. Date: Jul. 26, 2012

(65) Prior Publication Data
US 2014/0035180 A1 Feb. 6, 2014

(30) Foreign Application Priority Data
Jan. 17, 2011 (IN) .............................. 106/DEL/2011

(51) Int. Cl.
*C07C 67/48* (2006.01)
*C11B 1/00* (2006.01)
(Continued)

(52) U.S. Cl.
CPC ............... *C07C 67/48* (2013.01); *A23L 1/3002* (2013.01); *A61K 36/28* (2013.01); *C07C 403/24* (2013.01);
(Continued)

(58) Field of Classification Search
CPC ...... C07C 403/24; C07C 67/48; C11B 1/104; B01D 11/0203
See application file for complete search history.

(56) References Cited

U.S. PATENT DOCUMENTS 4,048,203 A 9/1977 Philip
4,466,923 A 8/1984 Friedrich
(Continued)

FOREIGN PATENT DOCUMENTS

EP 2119763 * 11/2009 ................ C11B 1/10

OTHER PUBLICATIONS

Scalia, S. et al., Analytical and preparative supercritical fluid extraction of Chamomile flowers and its comparision with conventional methods, 1999, Journal of Pharmaceutical and biomedical analysis, vol. 21, pp. 549 558.*

(Continued)

*Primary Examiner* — Yate K Cutliff
(74) *Attorney, Agent, or Firm* — Allen, Dyer, Doppelt, Milbrath & Gilchrist, P.A.

(57) ABSTRACT

A single stage straight forward process for extraction and isolation of lutein ester from the dried petals of marigold flowers *Tagetes* species using the carbondioxide as the supercritical fluid was developed. The pressure maintained for the extraction was up to 625 bar and at temperature up to 750 Centigrade. Lutein ester of high strength and purity up to 70% was achieved for the first time in single stage from the dried petals of marigold flowers-*Tagetes* species while enrichment of the lutein ester content up to 98% was achieved by crystallization of the lutein ester obtained from supercritical carbon dioxide extract (SCFE). The high strength and purified lutein ester isolated by supercritical fluid-single stage extraction process are free from saturated fat, oil, waxy impurities and serve as a safe source of nutritional supplement for human consumption and color additive for human foods.

8 Claims, 4 Drawing Sheets

(51) Int. Cl.
    *A23L 1/30* (2006.01)
    *A61K 36/28* (2006.01)
    *C07C 403/24* (2006.01)
    *C11B 1/10* (2006.01)

(52) U.S. Cl.
    CPC . *C11B 1/00* (2013.01); *C11B 1/104* (2013.01); *A23V 2002/00* (2013.01); *A61K 2236/00* (2013.01); *C07C 2101/16* (2013.01)

(56) References Cited

U.S. PATENT DOCUMENTS

| | | |
|---|---|---|
| 4,493,854 A | 1/1985 | Friedrich et al. |
| 4,511,508 A | 4/1985 | Vollbrecht et al. |
| 4,632,837 A | 12/1986 | Schutz et al. |
| 4,667,088 A | 5/1987 | Kramer et al. |
| 5,382,714 A | 1/1995 | Khachik |
| 5,648,564 A | 7/1997 | Ausich et al. |
| 6,106,720 A | 8/2000 | Kanel et al. |
| 6,191,293 B1 | 2/2001 | Levy |
| 6,689,400 B2 | 2/2004 | Majeed |
| 6,737,552 B1* | 5/2004 | Crombie .................... 568/816 |
| 6,909,021 B2 | 6/2005 | Crombie |
| 2004/0055954 A1 | 3/2004 | Sadano et al. |
| 2004/0220432 A1* | 11/2004 | Crombie .................... 568/824 |
| 2004/0267033 A1 | 12/2004 | Rao et al. |
| 2005/0244518 A1* | 11/2005 | Huang et al. ............... 424/736 |
| 2005/0266132 A1 | 12/2005 | Temelli et al. |
| 2009/0011112 A1* | 1/2009 | Marentis .................... 426/601 |
| 2009/0247633 A1 | 10/2009 | Crombie |
| 2010/0136190 A1* | 6/2010 | Bork et al. ................. 426/417 |

OTHER PUBLICATIONS

Reverchon et al., "Supercritical Fluid Extraction and Fractionation of Natural Matter," Journal of Supercritical Fluids, vol. 38, Mar. 2006, pp. 146-166.

Catchpole et al., "The Extraction and Fractionation of Specialty Lipids Using Near Critical Fluids," The Journal of Supercritical Fluids, vol. 47, 2009, pp. 591-597.

* cited by examiner

Fig.3

| Extraction No. | RM Source Code | Loaded Qty. of RM (Kg) | RM Analysis Lutein ester % | RM Analysis Moisture % | RM Analysis Lutein ester Content in RM (Kg) | Extraction Condition# Extractor (bar/°C) | Extraction Condition# Seperator-1 (bar/°C) | Extraction Condition# Seperator-2 (bar/°C) | Extraction Condition# Seperator-3 (bar/°C) | Lutein Ester Extract Yield (Kg) Seperator-1 | Lutein Ester Extract Yield (Kg) Seperator-2 | Lutein Ester Extract Yield (Kg) Seperator-3 | Lutein Ester Extract Yield (Kg) Seperator-1 + Seperator-2 (Extract Kg) | Lutein ester Assay in Extract % Seperator-1 | Lutein ester Assay in Extract % Seperator-2 | Lutein ester Assay in Extract % Seperator-3 | Lutein ester content (Kg) Seperator-1 | Lutein ester content (Kg) Seperator-2 | Lutein ester recovery % | Unrecovered Lutein (%) ester in exhausted flower meal | Unrecovered Lutein ester % compare to initial RM † |
|---|---|---|---|---|---|---|---|---|---|---|---|---|---|---|---|---|---|---|---|---|---|
| 001-008 | EBMG003 | 778 | 4.64 | 6.0 | 36.09 | 540/70 | 200/65 | 70/50 | 45/10 | 54.90 | 52.0 | T | 106.9 | 47.37* | 6.11 | NA | 26.01 | 3.18 | 80.85 | 0.62 | 10.77 |
| 009-011 | | 291 | 4.64 | 6.0 | 13.5 | 540/70 | 225/65 | 70/45 | 45/10 | 16.3 | 15.6 | T | 31.9 | 59.90 | 10.0 | NA | 9.76 | 1.56 | 83.8 | 0.36 | 9.14 |
| 012-013 | | 196 | 4.64 | 6.0 | 9.08 | 535/70 | 250/65 | 70/40 | 45/10 | 9.4 | 18.9 | T | 28.3 | 57.60 | 9.3 | NA | 5.41 | 1.75 | 78.85 | 0.61 | 10.29 |
| 014-019 | | 590 | 4.64 | 6.0 | 27.36 | 535/70 | 250/65 | 70/40 | 40/10 | 33.3 | 42.8 | T | 76.1 | 52.80 | 8.44 | NA | 17.58 | 3.61 | 77.44 | 0.38 | 15.81 |
| 020-024 | | 476 | 4.64 | 6.0 | 22.08 | 535/70 | 250/65 | 70/40 | 40/10 | 26 | 44.73 | T | 70.73 | 58.28 | 3.9 | NA | 15.15 | 1.74 | 76.26 | 0.66 | 11.85 |
| 025-029 | | 488 | 4.64 | 6.0 | 22.62 | 535/70 | 250/65 | 70/40 | 40/10 | 29.6 | 26.6 | T | 56.2 | 57.74 | 6.09 | NA | 17.09 | 1.62 | 75.59 | 0.91 | 6.49 |
| 055-059 | | 485 | 4.64 | 6.0 | 22.48 | 625/70 | 275/65 | 60/35 | 40/10 | 23.75 | 32.7 | T | 56.45 | 69.86 | 8.44 | NA | 16.55 | 2.75 | 85.85 | 0.32 | 8.38 |
| 060-062 | | 237 | 4.64 | 6.0 | 11.0 | 625/70 | 275/60 | 60/35 | 40/10 | 12.5 | 7.05 | T | 19.55 | 70.19 | 11.62 | NA | 8.77 | 0.81 | 87.09 | 0.22 | 8.16 |

Pressure & temperature varies with ± 5% of set parameters on PLC (Programmable logic controller)
*Lutein Ester Assay is low due to sticking losses of initial batches.
† Includes unaccountable degradation & handling loss
RM= Raw Material dry marigold flower meal, T= Traces, NA= Not applicable

SINGLE STAGE LUTEIN ESTER EXTRACTION FROM TAGETES SPECIES-MARIGOLD FLOWER MEAL

FIELD OF THE INVENTION

The present invention relates to a single step toxic-solvent free green commercial process.

BACKGROUND

U.S. Pat. No. 4,632,837 to Erwin Schultz et al. describes a process for the extraction of lutein from plants as Dill, Terragon leaves, *Cassia* buds and *Mimosa* flowers using supercritical carbon dioxide at 0° C. to 40° C. and a pressure of 80-200 bar. Separation of the resultant extract was achieved by dissolving it in diethyl ether or pentane at 20-60 bar and 0° C. to 20° C. The process is distinguished by the low pressure extraction and separation using the solvent and is not specific for *Tagetes* species-marigold flower.

U.S. Pat. No. 6,106,720 to J. S. Kanel et al

The process uses fluid/dense gas extraction of carotenoid from brine containing algae, carrot juice and tomato skin under enhanced solubility conditions comprising flowing a supercritical fluid carbon dioxide pre-saturated with water in a column up to 677 bar and 101° C. The process is distinguishable by extracting the total carotenoids.

U.S. Pat. No. 5,382,714 to F. Khachik

The process for isolation, purification and re-crystallization of lutein from saponified marigold oleoresin comprising the mixing of a saponified marigold extract with an alcohol/water mixture, lowering the temperature to precipitate lutein crystals, washing the crystals with water. The processing is distinguishable by using the saponification and organic solvents.

U.S. Pat. No. 4,048,203 to T. Philip

Purification of lutein fatty acid esters from marigold flower petals or its oleoresin was achieved by using alkanols. This process is distinguished for the use of alkanols.

U.S. Pat. No. 4,466,923 to J. P. Friedrich

The lipid containing materials such as vegetable seed, cereal seed germ and animals meat are extracted for lipids by simultaneous application of temperatures 40-80° C. and pressures up to 1033 bar. The process is distinguishable for the recovery of lipids.

U.S. Pat. No. 4,493,854 to J. P. Friedrich et al.

This process describes the process for defatting of the soybeans products

U.S. Pat. No. 4,511,508 to H. R. Vollbrecht et al.

The process for drying natural extracts of hop pellets, fresh hops and chamomile blossoms by using supercritical fluid extraction technology has been described. The process is distinguished by drying process of the herbal materials.

U.S. Pat. No. 6,689,400 to Majeed Muhammed

The present invention concerns methods of obtaining stable lutein and its derivatives. Additionally, the invention concerns various compositions comprising lutein, lutein esters, tetrahydrocurcuminoids, and carnosic acid. The process of invention is about mainly extraction of marigold flowers using solvent alcohol and stabilization of obtained lutein using with a stabilizing mixture of tetrahydrocurcuminoids and curcuminoids.

PCT/IB01/02057 and U.S. Patent Publication No. 20040267033 to J. R. Rao et al.

A two stage process for the extraction of lutein diester to achieve 10-15% lutein diester in first stage has been described by using 200-350 bar pressure and 40-80° C. temperature. Lutein diester up to 20-25% has been only achieved in the second stage while the purification of lutein. The process is distinguished by low purity lutein diester, 10-15% in first stage and 20-25% in second stage and has been achieved only by using two stage process and the process parameters like pressure 200-350 bar, temperature 40-80° C. for the first stage and 60-140 bar, 15-25° C. were maintained in the second stage.

U.S. Pat. No. 6,909,021 to Lance B. Crombie.

The invention provides a method for extracting carotenoids from green plant materials using supercritical fluid extraction. A first and second supercritical fluid extraction is performed on the green plant composition at two different pressures to obtain two extracts. The first extract includes substantial amounts of .beta.-carotene. The second extract may have a controlled concentration of .beta.-carotene, and includes substantial amounts of lutein. This patent is mainly distinguished by method for extracting mixed carotenoids β-carotene with lutein from green plant alfalfa dry juice curd but not of specific marigold flower meal lutein ester.

U.S. Patent Publication No. 20090247633 to Lance B. Crombie

A method for the separation of carotenoids, especially lycopene, from fruits and vegetables, especially tomatoes. A mixture of powdered fruit and/or vegetable and an edible oil is subjected to supercritical-$CO_2$ fluid extraction. A mixture of the oil and lycopene is separated. Lycopene of food grade quality is obtained. This patent mainly distinguished by method for extracting mixed carotenoids between 30-40 weight % lutein with β-carotene and fatty acids from green plant alfalfa dry protein curd but not of specific marigold flower meal lutein ester. Also finally the obtained carotenoids with fatty acids are formulated with cyclodextrin in ethanol medium.

U.S. Patent Publication No. 20050266132 to Temelli, Feral et al.

A method for separating carotenoids from carotenoid-containing material comprising sizing a carotenoid-containing material, passing a mixture of oil and supercritical $CO_2$ (SC—CO2) continuously through the carotenoid-containing material at conditions effective to extract a carotenoid into the mixture of oil and SC—$CO_2$, and collecting the carotenoid-containing oil. The invention described is mainly about the extraction of carotenoids specifically β-carotene from carrot on lab scale with SCF—$CO_2$ pressures of less than 510 bar in presence of canola oil as co-solvent.

During the past decade, many persons have identified, and quantified carotenoids from fruits and vegetables commonly consumed. These studies have revealed that as many as 40 to 50 carotenoids may be available from the diet and absorbed, metabolized, or utilized by the human body (Khachik et al. 1991, Pure Appl. Chem., 63: 71-80). However, among these, only 13 carotenoids and 12 of their stereoisomers are routinely found in human serum and milk (Khachik et al. 1997, Anal. Chem. 69:1873-1881). In addition, there are 8 carotenoid metabolites and one stereoisomer in human serum or plasma which results from a series of oxidation-reduction reactions of three dietary carotenoids namely lutein, zeaxanthin and lycopene. These metabolites were first isolated and characterized by Khachik et al. (1992, Anal. Chem. 64: 2111-2122). In another study, the ingestion of purified supplements of dietary (3R,3'R,6'R)-lutein and (3R,3'R)-zeaxanthin was shown to, not only, result in an increase in the blood levels of these compounds in humans but also increased the concentration of their oxidative metabolites in plasma (Khachik et al. 1995, J. Cellular Biochem. 22: 236-246).

Bone et al. (1985, Vision Res. 25: 1531-1535; 1993, Invest. Ophthalmol. Vis. Sci. 34: 2033-2040) demonstrated that the human macular pigment is a combination of lutein and zeaxanthin and speculated that these dietary carotenoids may play an important role in the prevention of eye disease namely, Age-Related Macular Degeneration (ARMD). This was later confirmed in a case-controlled epidemiological study in which the high consumption of fruits and vegetables, rich specifically in lutein and zeaxanthin, was correlated to a 43% lower risk of ARMD (Seddon et al. 1994, J. Am. Med. Assoc. 272: 1413-1420). More recently, in addition to lutein and zeaxanthin, the author and his co-workers reported the isolation and identification of one major and several minor oxidation products of lutein and zeaxanthin in human and monkey retinas (Khachik et al. 1997, J. Invest. Ophthalmol. Vis. Sci. 38: 1802-1811)

Although lutein and zeaxanthin is obtained from certain fruits and vegetables, the isolation of lutein from extracts of marigold flowers proves to be most economical. In Marigold flowers lutein is the major carotenoid and is normally accompanied by about 3-6% zeaxanthin; in Lycium Chinese Mill (LCM) berries zeaxanthin is the major carotenoid and is completely free from lutein. Purification of lutein esters from marigold flowers was patented by Philip in 1977 (U.S. Pat. No. 4,048,203). The purified lutein esters by humans, upon ingestion, these compounds partially undergo hydrolysis in the presence of pancreatic secretions in the small intestine to regenerate free lutein which is then absorbed [Khachik et al. Pure & Appl. Chem., 63(1): 71-80, 1991].

A method for the purification of free lutein from extracts of marigold was first reported in 1991 [Tyzkowski and Hamilton, Poultry Sci., 70(3): 651-654, 1991]. However, this method was extremely time-consuming, uses harmful organic solvents, produced poor yield and it could not be a viable solution for commercial production.

In view of the important biological activity of lutein and zeaxanthin, one author developed a process for isolation, purification, and recrystallization of lutein from saponified marigold oleoresin which was patented in 1995 (Khachik, U.S. Pat. No. 5,382,714). The saponified marigold oleoresin was obtained from Kemin Industries (Des Moines, Iowa) and is normally prepared by extraction of dried Marigold petals with n-hexane, followed by saponification and solvent evaporation. To date, this process is the only available method for isolation and purification of lutein (containing 3-6% zeaxanthin) from marigold with purity greater than 97%. Later, another process for the isolation of lutein from a saponified marigold oleoresin has been reported wherein lutein can be obtained with 70-85% purity (U.S. Pat. No. 5,648,564, 1997). This process employs propylene glycol (40.9%, weight percent) and an aqueous alkali (18.2%, weight percent) to saponify hexane extract of dried marigold petals (marigold oleoresin, 40.9%, weight percent) containing lutein esters at 70° C. in 10 hours.

There are several major disadvantages with in listed processes; these are discussed as follows. The marigold oleoresin is prepared by extraction of dried marigold petals by boiling with n-hexane for extended time period. Since carotenoids in general, are sensitive to prolonged heat, this procedure can result in degradation or isomerization of these compounds.

The hydrolysis of lutein esters in the marigold oleoresin is generally conducted using aqueous solution along with alcohol and propylene glycol in which the fatty acid esters of lutein and zeaxanthin have very low solubility. As a result, this process requires high temperature up to 70° C. and 10 hours to complete the saponification. This can once again result in the degradation and isomerization of lutein and zeaxanthin.

Due to the high viscosity of propylene glycol, during handling and several purification steps, the saponified product is more subjected to high temperature ranging from 70 to 85° C. Exposure to heat in the presence of atmospheric air may result in oxidative degradation of carotenoids and formation of a number of the side products. In summary, the above patented process (U.S. Pat. No. 5,648,564) employs extraction and saponification of marigold flowers for lutein ester and lutein in two separate steps, followed by several purification steps. According to the authors, when the extraction and saponification steps were combined to simplify the procedure, the result was 64.7% reduction in the yield of lutein in comparison to the two-step extraction and saponification processes described by Khachik. Overall, these procedures are quite time-consuming and are carried out under harsh conditions and produces lutein with only 70-85% purity.

The earlier patent by the inventor (Khachik, U.S. Pat. No. 5,382,714) generally has limitations. This process also uses n-hexane as the extracting solvent and, at the last purification step, it employs dichloromethane and n-hexane as the recrystallization solvents to obtain lutein, containing 3-6% zeaxanthin, with purity of 97% or greater. Since according to the FDA, the use of dichloromethane and hexane in drug and food products should be limited and the lutein purified by these solvents should be thoroughly dried under high vacuum to remove residual solvents.

The patents and literature under the prior art have methods of search for developing purified free lutein or lutein esters and used principally several complex methods involving the use of hydrocarbon toxic solvents, chlorinated solvents and other hazardous chemical substance treatments so to make lutein either from marigold flower or green protein or juice concentrates. Also the methods of supercritical extractions earlier attempted in the arts either has first used the organic solvents followed by subsequent process of supercritical fluid extraction or two stage supercritical carbondioxide extraction process wherein the refined extracts have very low concentrations of lutein ester of limited use for making direct useful high percentage food, beverage and pharmaceutical variant forms like oil soluble dispersions, beadlets, granules or powders. Current investigation is taken as first ever art, superseding the drawbacks of previous investigations, in order to develop very high strength or purified lutein ester from marigold flower meal using a straight forward one stage very high pressure commercial supercritical extraction system which is facilitated with an advanced multiple-three product collection separator design. The three separator design facilitated SCF—$CO_2$ system makes the extraction much simpler than the prior art methods to develop high strength and purity lutein ester which is used for making directly useful high percentage food, beverage and pharmaceutical variant forms like oil soluble dispersions, beadlets, granules or powders.

SUMMARY OF THE INVENTION

An extraction process for the extraction of lutein ester from marigold dry flower meal was developed for the first time by adopting a high pressure Supercritical Fluid Carbondioxide Extraction process at pressures up to 625 bar and temperature up to 75° C. in single stage using advanced multi-stage three separator system. In single stage extraction, the highest concentration of lutein ester achieved was up to 70% with a maximum recovery of 87%. The obtained extraction recovery of lutein ester from marigold dry flower meal at pressure conditions above 500 bar is almost constant without much variations and optimum pressure for the lutein ester extraction recovery was found to be 540 bar with lutein ester content of about 60%. However at high pressure 625 bar, there was slight increase in the recovery with higher lutein ester extraction content. The lutein ester recovery results from dry marigold flower meal are given in FIG. 1. The lutein ester extract of 40-70% obtained by straight forward single stage SCF—CO2 extraction process is used as source material for furthest enhancement of lutein ester to 90-98%. Also the high percentage and purity lutein ester extract obtained mainly from SCF—$CO_2$ extraction process are much useful for direct formulation to make variant dosage forms like beadlets, powders, granules and oil soluble-dispersions of food, beverage or pharmaceutical interest.

BRIEF DESCRIPTION OF THE DRAWINGS

FIG. 3 is a table of recovery of lutein ester and its concentration from dry marigold flower meal by single stage process of SCF—$CO_2$ extraction process System, according to the present disclosure.

DETAILED DESCRIPTION OF THE INVENTION

Figure 1:
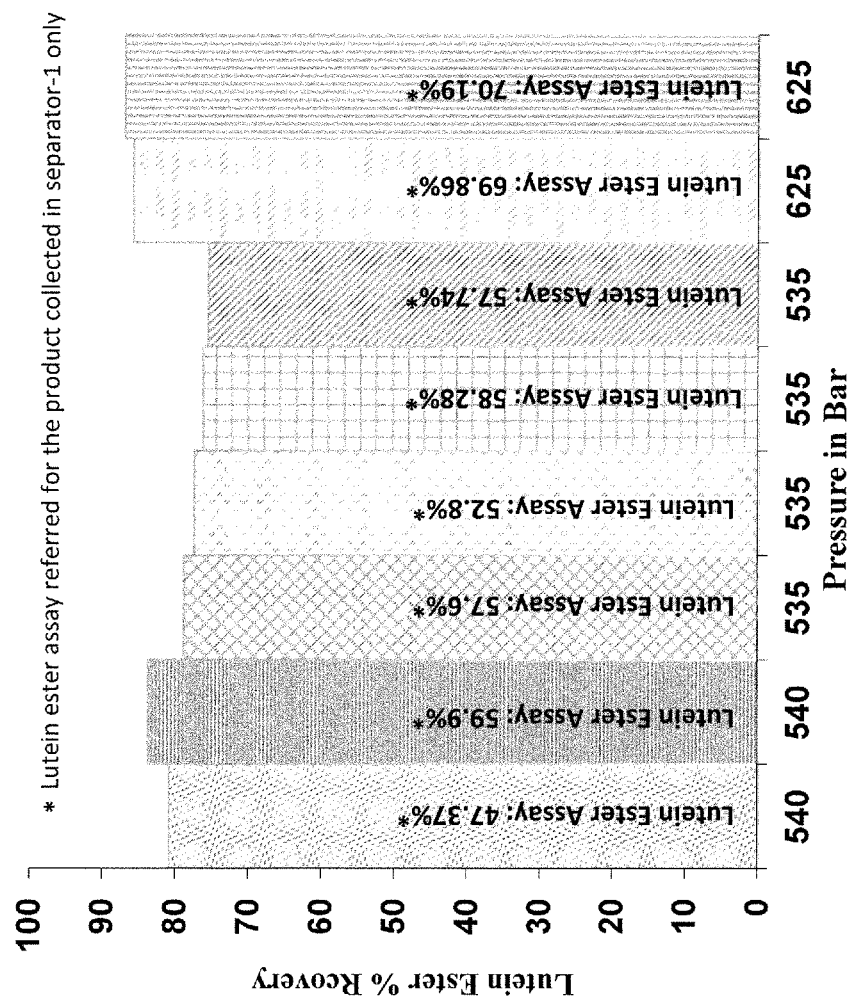
FIG. 1 is a chart of recovery of lutein ester and its assay content from dry marigold glower meal, according to the present disclosure.

The present invention relates to a single step toxic-solvent free green commercial process developed for the first time for extraction, isolation, and purification of lutein ester of very high strength and purity from marigold flowers using industrial supercritical fluid carbondioxide extraction system of 3×300 liters extractors which are facilitated with multiple-three separator product collection system.

The invention wherein a commercial extraction process is developed for the first time to produce a very high percentage and purity lutein ester extract up to 70% from marigold flower meal. Most importantly, the invention addresses and supersedes all the disadvantages, with regard to all previously patented procedures described, as a straight forward method to get, on a single stretch, lutein ester up to 70% which is never achieved by any patented methods, without use of toxic organic solvents, using only green toxic free-solvent carbondioxide. The method of invention has better advantage for the extraction of very high strength and purity lutein ester in much more simple fashion in single strength and is only possible by very high pressure supercritical carbondioxide extractor system that is now facilitated with advanced multiple-three separator product collection system than the reported method of extraction of lutein ester, of very low strength and purity, that is normally produced by two stage liquid-liquid extraction and dual separator system. The invention of method also produced a high percentage lutein ester by single stage supercritical extraction eliminating the use of complex methods like extraction with hydrocarbon toxic solvents, use of chlorinated solvents and drastic hazardous chemical reactions which derive free lutein instead of lutein ester and the later has much better proven stability and bio-availability than chemically derived free lutein. The high strength supercritical fluid extracted lutein ester extracts of 70%, of toxic solvent free, having better purity are very well used in preparing different variant forms by blending with diluents or excipients to get 5-40% as oil soluble liquid dispersions, beadlets, powders and granules as best alternative preparations to solvent process products used for food, beverage and dietary supplement applications. While the preparation of high food, beverage and pharmaceutical variants of 20-40% lutein ester in the form of oil soluble dispersions, beadlets, powders or granules is not possible from the low percentage or purity lutein ester extracts derived from two stage processed supercritical fluid extraction process.

Current investigation is taken as first ever art and the invention is a straight forward one stage very high pressure supercritical extraction process method to get unusually very high strength lutein ester when compared to previous arts wherein the previous art of invention, of supercritical fluid process method, has never achieved high strength lutein ester extracts. The straight forward single stage method of current investigation without adopting any two stage SCF—$CO_2$ process liquid-liquid extraction has lead to produce high strength lutein ester which could never be possible unless an SCF—$CO_2$ system used have multiple-three separator collection system than those of conventionally designed dual collection separators. A three separator collection system that is well designed in current search becomes one of first ever key feature. One of such major process key feature of the system is dynamic balancing of the process parameters between product collection separators and enrichment of product lutein ester. Further low strength lutein ester extracts obtained in dual collection separator systems are never useful to produce convenient variant dosage forms of high percentage like 20-40% oil soluble dispersions, beadlets, powders or granules being used in food, beverage and pharmaceutical applications. The previously reported other arts also have used combustive and complex chemical methods that are either using, organic hydrocarbon carbon solvents, chlorinated solvents and hazardous chemical reactions, two stage supercritical fluid carbondioxide extractions or integrated methods thereof. The two stage supercritical method of extraction has limitation to achieve higher strength and purity lutein ester due to use of two stage liquid-liquid extraction process of supercritical fluid system having dual collection separators where process parameter simulation mimics are never possible. While to compare the current investigation with previous art, the achievement of high strength and purity lutein ester extracts of commercial interest are possible in single, simple, straight forward process by a provision of a facility provided as three-multiple separators connected in series to the parallel extractors of supercritical fluid carbondioxide extraction system. Also the high percentage lutein ester extracts obtained by supercritical extraction process under current invention are further useful for penultimate refining process in one-go avoiding complex, combustive multiple solvent stage processes, of prior arts, to get very high percentage crystalline powder of lutein ester of 90-98%. Overall two of the major investigation processes of present investigation was to make lutein ester of high percentage in very simple and cost effective fashion are never done by any of prior arts.

The process that was investigated now describes a single stage commercial extraction methodology, never disclosed in any of referred prior arts, using very high pressure SCF—$CO_2$ extraction facility with new design of multiple-three separators. This includes respectively high, medium and low pressure separators which are connected in series to the multiple-three parallel extractors of 300 L each. High pressure extractors are designed independently as parallel systems connected each to independent high pressure CO2 pumps having CO2 flow rate up to 45 Kg/min with a design pressure of both pumps and extractors 690 bar while the respective H.P, M.P and L.P separators are designed to pressures of 450, 240 and 83 bar. The extraction of marigold flower meal in powder form of 2-3 mm particle size was conducted by placing the meal in a basket which was further loaded into an extractor vessel. In the process of extraction, the extractors are confined to various extraction pressures between pressures of operation 530-625 bar while temperatures are controlled through heat exchangers. The pressure parameters of each extractor and separators are regulated to maintain the set pressure conditions by high pressure auto control vales in concordance of temperatures regulation through heat exchangers. In principle the extraction of lutein ester from flower meal is carried by supercritical fluid carbondioxide that is acting as dense fluid or solvent takes away the lutein ester from flower meal particle through diffusion and the lutein ester in dissolved condition in supercritical fluid is pushed to the H.P separator first. An investigation was conducted wherein the multiple separators are very much crucial in enhancing the lutein ester content up to 70% as single stage process which was achieved by varying the pressures bar and temperatures OC of respective H.P, M.P and L.P. separators individually between 350 and 60, 130 and 60, 40 and 12. The multi (three) separator SCF—$CO_2$ system allows to change the pressures and temperatures to a broad margin so that allowing for, simultaneously at single stretch, the removal and push of unwanted waxes, oils present in the marigold oleoresin lutein ester collected in the H.P. in to M.P. and L.P separators thus enrich the lutein ester content to 70% in H.P. separator. In a dual separator systems which are conventionally designed will not allow for broad variations in pressure and temperature combination selection between two separators for the removal of unwanted waxes. In the investigation as an instance that a dual separator system designed at extraction and separation pressures as inferred in patent, U.S. Patent Publication No. 20040267033 to J. R. Rao et al., where the maximum extraction pressure carried at 475 bar will able to produce the lutein ester content maximum 15% which is normally very low when compared to current investigation. While in the three separator SCF—$CO_2$ system simultaneous extraction, refining and enhancement of lutein ester takes place unlike the two stage supercritical extraction process while in the first stage primary extraction and second stage liquid-liquid extraction processes are independently conducted on a dual separator system to achieve low lutein ester contents of 25% only. That means a process in dual separator supercritical system first adopts a first stage primary extraction to get lutein ester 15%, of normally low strength, which is then re-extracted by second or two stage liquid-liquid extraction to get still low percentage lutein ester extract of 25%. The content of lutein ester obtained in dual separator SCF—$CO_2$ system is low due to richness of waxes and lighter oils of marigold flower seed. It is possible one to control the unwanted waxes and fatty oils in the extract of lutein ester only by controlling the parameters dynamically between well designed separator systems. In case of two separators SCF—$CO_2$ system dynamic process parameter controlling is not possible. Wherein the three separator SCF—$CO_2$ system the parameter of first H.P. separator is maintained between 275-350 bar at 60° C. so that waxes and lighter oils collected with lutein ester during extraction in the first separator are simultaneously carried in dissolved form by supercritical fluid to second M.P separator. Thus avoids the second stage liquid-liquid extraction as reported in prior art. A pressure condition maintained, if, 275-350 bar at 60° C. in first separator of dual separator system, will not allow to retain the pressure conditions in second separator less than 55 bar which is equivalent to the receiver pressure necessary for recovery and recycling of CO2 into extractor. A pressure required in separator two to collect and retain the unwanted waxes and oils that are removed from lutein ester extract of first separator to be at least between 70-130 bar at temperatures of 40-60° C. Otherwise conditions that are commonly designed for final recovery and recycling of CO2 in separator two of dual separator SCF—$CO_2$ system will carry the waxes and oils to the receiver and re-carry the material to the extractor vessel thus making the extraction process always incomplete. Thus second and third separators as in case of three separator system are must to enrich the extract without carry of any liquid-liquid extraction at one stretch with high lutein ester content. Otherwise one has to re-extract by two stage or second stage extraction process called liquid-liquid extraction using dual separator SCF—$CO_2$ system to get high lutein ester content. Also low lutein ester concentrations achieved from dual separator system are further carried for liquid-liquid extraction will not make a possibility to enrich the lutein ester more than 25% as compared with the single stage extraction of three separator system which can produce very high lutein ester in single stretch up to 70%. Thus a process of investigation, using single stage SCF—$CO_2$ extraction system constituting dynamic three separators, is a new, never carried search to get very high strength lutein ester in single stage SCF—$CO_2$ extraction.

Most importantly, this process addresses and supersedes all the disadvantages with regard to all previously patented procedures described above as a straight forward method to get, on a single stretch, lutein ester up to 70% which is never achieved by any patented methods, without use of toxic organic solvents, using only green toxic-free solvent carbondioxide. As a result of the current investigation wherein the lutein ester from marigold flower meal obtained by supercritical fluid extraction process becomes a source material and useful to refine further in very much easy and simpler fashion without much complicated processes as described in several other patents in a purity of 90% or greater and is also therefore suitable for human consumption. The high strength supercritical fluid extracted lutein ester extracts of 70%, of toxic solvent free, having better purity are very well used in preparing different variant forms by blending with diluents or excipients to get 5-40% as oil soluble liquid dispersions, beadlets, powders and granules as best alternative preparations to solvent process products used for food, beverage and dietary supplement applications. Also obtaining the higher percentage extracts by single stage supercritical extraction avoids the use of complex methods like extraction with hydrocarbon solvents, use of chlorinated solvents, drastic hazardous chemical reactions to get free lutein instead of lutein ester which has much better proven stability and bioavailability than chemically derived free lutein.

Examples

Figure 2:
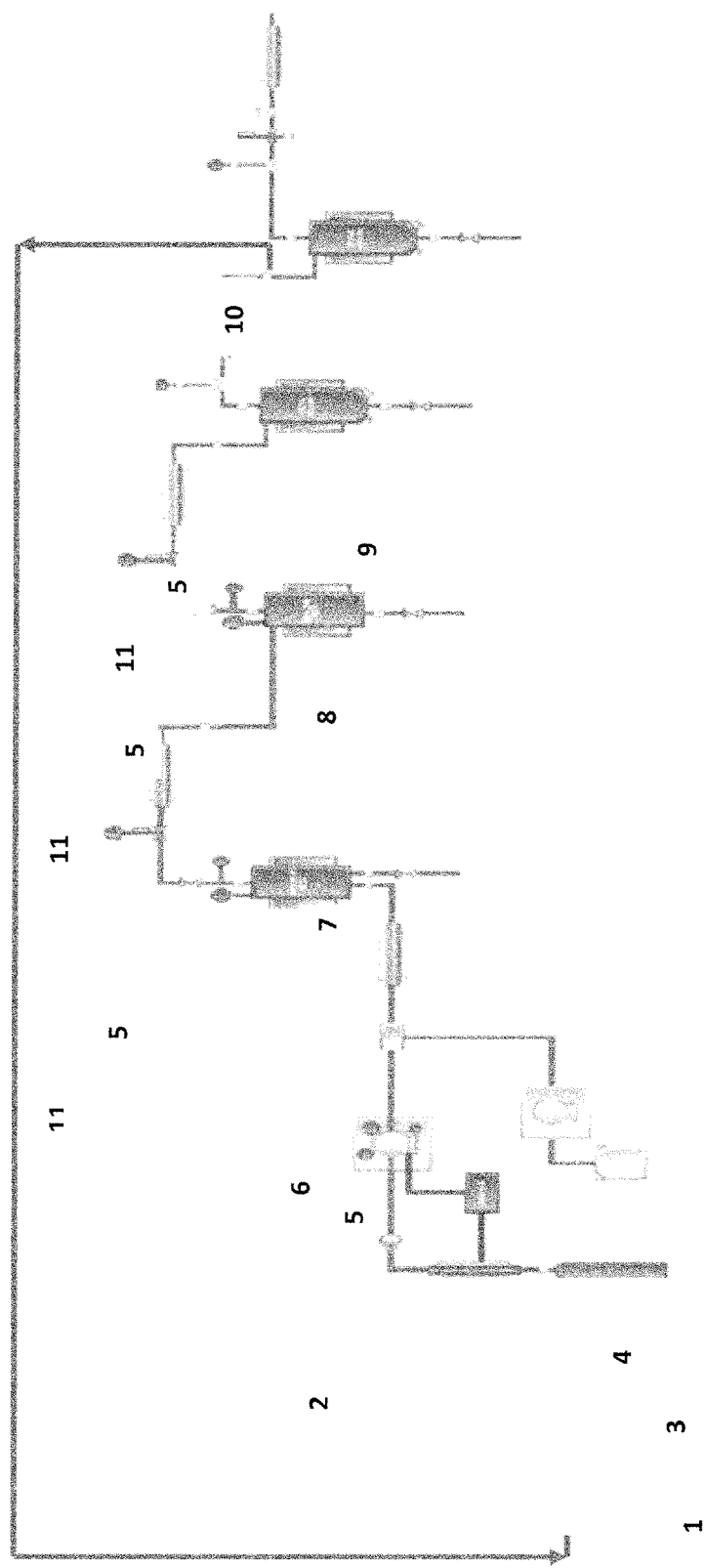
FIG. 2 is diagram of SCF—$CO_2$ extraction processors, according to the present disclosure.
Figure 4:
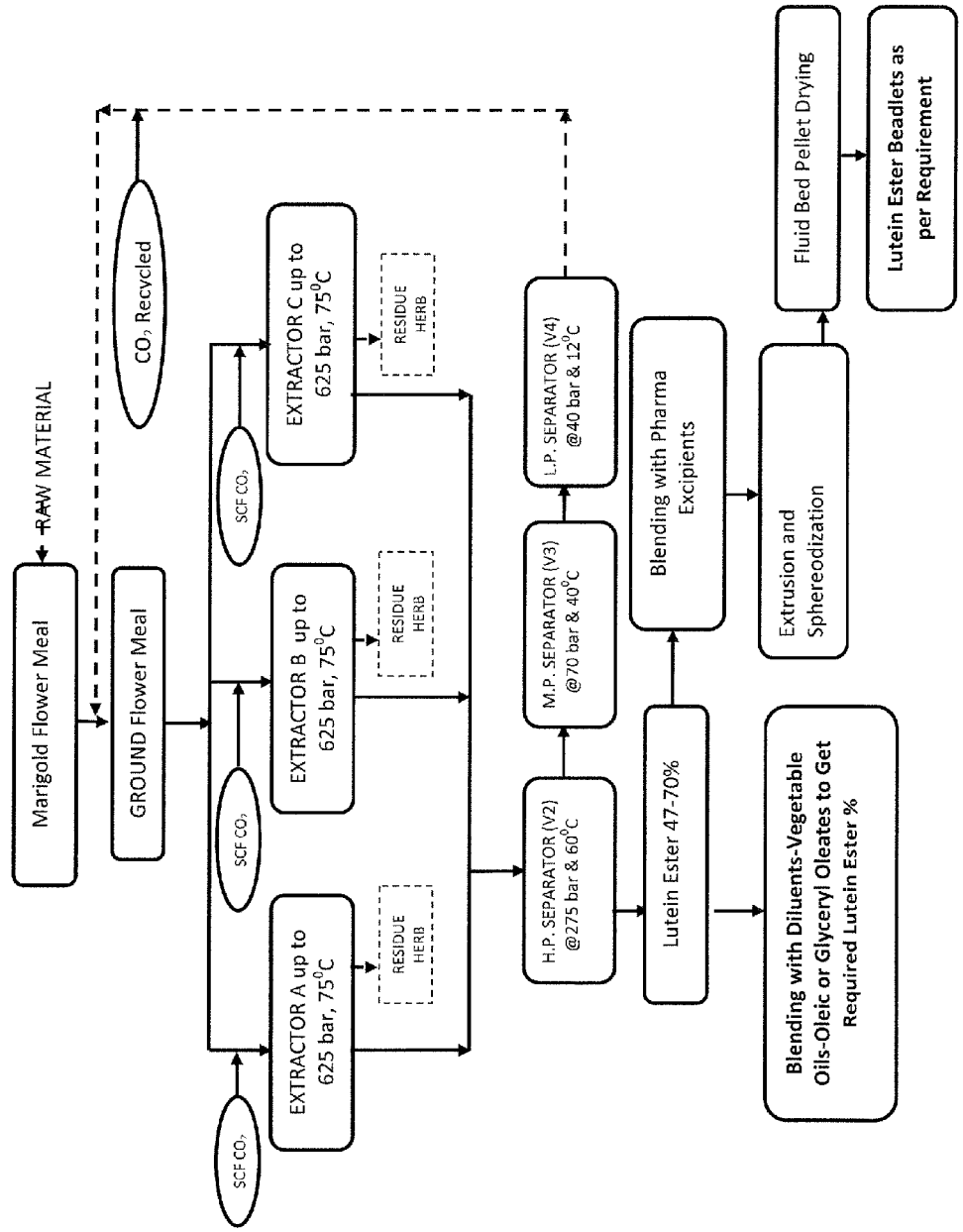
FIG. 4 is a flowchart for the SCF—$CO_2$ extraction process, according to the present disclosure.

1. The multiple-three extractor supercritical CO2 extraction system (FIG. 2) with the capacity of 300 L×3 vessels was used for the extraction. In FIG. 2, 1=CO2 tank, 2=CO2 Pump, 3=Co-Solvent tank, 4=Co-Solvent pump, 5=Heat Exchanger, 6=(Extractor)$^n$, n=3, 7=Separator 1, 8=Separator 2, 9=Separator 3, 10=Cooling Condenser. The basket was filled with dry marigold flower meal (about 2-3 mm particle size) up to 85-125 kg in basket, till the basket is full. The top basket cover plate was assembled properly with basket seal. Basket bottom and top plate shall be assembled with filter paper Whattman No. 1 along with mesh to avoid fine materials should not carry to the separator vessels. In the experiment, very much broad changes were made in pressure bar and temperature ° C. of respective multiple H.P, M.P and L.P separators individually between 350 and 60, 130 and 60, 40 and 12. At the end the optimized extraction parameters were set on programmed logic control (PLC) system for extractors (bar/° C.) 625/70° C., high pressure separator 275/60° C., medium pressure separator 70/40° C. and low pressure separator 40/12° C. and also carried the experiments at various conditions tabulated in FIG. 3 with process flow FIG. 4

The flow rates of CO2 on the pumps are set for 10-30 kg/min. Set $CO_2$ flow for each extractor 60±10% kg/kg of the raw marigold flower powder meal loaded. Start $CO_2$ pump with 10 kg/min and the flow rate was gradually increased up to 30 kg/min by observing pump run is in healthy condition. Collect water from low pressure separator every 30 minute. Collect lutein ester extract from H.P and other lower color lutein ester fraction and or waxes, oil from M.P and L.P separators. Also water was collected, separately, from medium pressure and low pressure separators.

Yields:

The extraction yield from dry marigold flower meal with respect to lutein ester content of flower meal>4% is given below. However lutein ester concentration values may vary on initial raw flower meal lutein ester content.

| | | Extraction Yield (On dry Marigold flower Meal basis) | Lutein ester content |
|---|---|---|---|
| 1) | High pressure separator | 3.0-7.0% | Assay 42-73% |
| 2) | Medium pressure separator | 3.0-8.0% | Assay 2-11% |
| 3) | Low pressure separator | <1.5% | Assay 5-10% |

2. The lutein ester 1.0 kg (assay approximately 40-70% of SCF—$CO_2$ extract as source material) was dissolved in 5 l isopropyl alcohol. It was occasionally stirred for 48-50 hours at temperatures 25-80° C. The stabilizer natural tocopherol 0.05% was added to the solution during the dissolution of the lutein ester extract. The material was filtered once clear orange crystals are developed. Wash the crystals using approximately 0.1 l of isopropyl alcohol. The resultant crystals were analyzed and the assay of crystals obtained is 90-98% of lutein ester. Yield: 4.5% (on dry Marigold flower meal basis) with average 90% lutein ester assay. Similarly various solvents like ethyl acetate, ethanol and methyl ethyl ketone and equal mixtures thereof were used independently, replacing isopropyl alcohol, to dissolve the marigold lutein ester in various ratios 2-15 volumes to that of lutein ester extract weight. Then the lutein ester dissolved was precipitated by adding isopropyl alcohol to make the isopropyl alcohol ratio 1:1 to that of other solvents or mixtures thereof specified here above. At all the stages 0.05% natural tocopherol was added as stabilizer to avoid the process degradation of lutein ester. The lutein ester crystals obtained were filtered and processed in similar manner referred above to get lutein ester of 90-98% assay.

3. Lutein ester soft extract (assay approximately 40-70%) was taken in a hot water/steam jacketed stainless steel vessel and heated at 50-60° C. for 40-60 minutes to make it liquid. The diluents like vegetables oil, glyceryl mono-oleate, medium chain triglyceride and mixtures thereof were added to dilute the extract for making it 5-40% lutein ester of flowable liquid. Rosemary extract (20% carnosic acid), natural tocopherol of 80% and mixtures thereof at respective concentrations 0.4 and 3% on weight of lutein ester extract were used as the stabilizers. To make 40% concentration of lutein ester, selected proportion of lutein extract of 70% lutein ester to diluent is 1:0.75.

4. Lutein ester extract (assay approximately 40-70%) was taken in stainless steel rotacoating pan of hot water jacket and then heated at 50-60° C. for 40-60 minutes to make it liquid. Rosemary extract (20% carnosic acid), vitamin C palmitate, natural tocopherol of 80% and mixtures thereof at respective concentrations 0.4, 0.5 and 3% on weight of lutein ester extract were used as the stabilizers. The excipients like AEROSIL®, starch ester, microcrystalline cellulose, hydroxy propyl methyl cellulose, light magnesium carbonate, tribasic calcium phosphate, magnesium stearate and mixtures thereof were added under jacket temperature of 60-70° C. and rotate the pan till the formation of perfect granular powder of 5-40% lutein ester concentration. To prepare 40% concentration of lutein ester, selected ratio of lutein ester extract of 70% lutein ester to excipients is 1:0.75.

5. Lutein ester soft extract (assay approximately 40-70%) was taken in a planetary mixer or rapid granulating mixer. The various excipients like starch ester, hydroxy propyl methyl cellulose, microcrystalline cellulose, silicon dioxide, natural tocopherol powder, rosemary extract, tribasic calcium phosphate, vitamin C palmitate and mixtures thereof were added to the ribbon blender. Rosemary extract (20% carnosic acid), vitamin C palmitate, natural tocopherol powder of 80% and mixtures thereof at respective concentrations 0.4, 0.5 and 3% on weight of lutein ester extract were used as the stabilizers. Stirred the total mass in a ribbon blender for 2 hours and added the reverse osmosis treated water (quantity sufficient) till to formation of damp mass. Pass the damp mass through extruder fitted 1 mm mesh and then the filaments or needles obtained from extruder were subjected for spherodization to get 1 mm beadlets of 5-20% lutein ester content. Excipient ratio selected to the lutein ester extract of 40% lutein ester to get 10% lutein ester beadlet is 2.8:1 while for 5% lutein ester beadlet is 5.6:1. The ratio of excipients selection for making 20% lutein ester beadlet from 60% lutein ester extract is 2.9:1.

INDUSTRIAL APPLICATION OF THE INVENTION

The investigation is a first ever developed industrial process using a supercritical fluid extraction system of 3×300 Liters extractors facilitated with advanced multi-separator system. The process has been developed as eco-friendly, green toxic-free recyclable carbondioxide fluid process and is single stage, straight forward process which full-out the drawbacks of previous processes which are normally developed utilizing combustive processes with complex toxic-organic flammable solvents or two stage extraction supercritical fluid process that produce very low strength and purity lutein ester extracts. The high strength and purity lutein ester developed is much cost-effective product derived by organic-green process and the product derived-off is much useful as alternate direct industrial ingredient for food, beverage and nutraceutical applications.

The invention claimed is:
1. A single stage simultaneous extraction and supercritical fluid carbon dioxide (SCF—$CO_2$) multi-separator refining and separation process of lutein ester from marigold flower meal, the process comprising:
feeding the marigold flower meal into extractors maintained at a pressure between 500-625 bar and a temperature less than or equal to 75° C.;

maintaining a flow rate of SCF—CO$_2$ into the extractors loaded with the marigold flower meal at 10 kg/min initially, and then increasing the flow rate up to 30 kg/min;

processing of extractor feed in series and into a high pressure separator, a medium pressure separator, and a low pressure separator, the high pressure separator, the medium pressure separator, and the low pressure separator operating at a pressure and temperature of 275-350 bar and 60° C., 70-130 bar and 40-60° C., 40 bar and 12° C., respectively;

collecting the lutein ester from the high pressure separator, the lutein ester having a purity of 40-70%, collecting a lower color lutein ester fraction from the medium pressure separator, and collecting waxes and oil from the low pressure separator.

2. The process of claim 1 further comprising additional refining of the lutein ester extract to a purity of 90-98%, the additional refining comprising:

dissolving the lutein ester in an isopropyl alcohol solution and stirring at room temperature;

adding stabilizer natural tocopherol to the isopropyl alcohol solution during the dissolving of the lutein ester; and filtering precipitated material once crystals are developed, and washing the crystals with isopropyl alcohol to obtain lutein ester with a purity of 90-98%.

3. The process of claim 2, further comprising adding at least one of ethyl acetate, ethanol and methyl ethyl ketone and to independently dissolve the lutein ester, and precipitating the lutein ester by adding isopropyl alcohol.

4. The process of claim 1, wherein the extractors are maintained 540 bar and 70° C.

5. The process of claim 1, wherein the the high pressure separator operates at 275 bar and 60° C.; wherein the medium pressure operates at 70 bar and 40° C.; and wherein the low pressure separator operates at 40 bar and 12° C.

6. The process of claim 1 further comprising obtaining oil soluble dispersion of 5-40% lutein ester by using triglycerides and vegetable oils and mixtures thereof with at least one of stabilizer rosemary extract, natural tocopherol and mixtures thereof.

7. The process of claim 1 generating powder form of the lutein ester by using at least one of aerosil, starch ester, microcrystalline cellulose, hydroxy propyl methyl cellulose, light magnesium carbonate, tribasic calcium phosphate, magnesium stearate and mixtures thereof.

8. The process of claim 1 further comprising generating lutein ester beadlets with a purity of 5-20% by using at least one of starch ester, hydroxy propyl methyl cellulose, microcrystalline cellulose, silicon dioxide, natural tocopherol powder, rosemary extract, tribasic calcium phosphate, vitamin C palmitate and mixtures thereof.

* * * * *